(12) United States Patent
Chen et al.

(10) Patent No.: US 7,404,932 B2
(45) Date of Patent: Jul. 29, 2008

(54) SOLID-PHASE NANO EXTRACTION DEVICE

(75) Inventors: Jin-Ming Chen, Hsinchu (TW);
Chien-Te Hsieh, Hsinchu (TW);
Yue-Hao Huang, Hsinchu (TW);
Rong-Rong Kuo, Hsinchu (TW);
Yu-Run Lin, Hsinchu (TW);
Chiung-Wen Hu, Hsinchu (TW);
Mu-Rong Chao, Hsinchu (TW);
Kuen-Yuh Wu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 828 days.

(21) Appl. No.: 11/004,820

(22) Filed: Dec. 7, 2004

(65) Prior Publication Data
US 2005/0142039 A1    Jun. 30, 2005

(30) Foreign Application Priority Data
Dec. 26, 2003    (TW) .............................. 92137210 A

(51) Int. Cl.
*B01L 11/00*    (2006.01)
*B01L 3/02*    (2006.01)
*G01N 1/18*    (2006.01)

(52) U.S. Cl. .................. 422/101; 422/100; 436/177
(58) Field of Classification Search ........... 422/99–101; 436/177
See application file for complete search history.

(56) References Cited

U.S. PATENT DOCUMENTS

| | | | | |
|---|---|---|---|---|
| 5,585,070 A | * | 12/1996 | Lessard et al. | 422/101 |
| 6,416,716 B1 | * | 7/2002 | Shukla et al. | 422/101 |
| 6,491,872 B1 | * | 12/2002 | Wick | 422/72 |
| 6,537,502 B1 | * | 3/2003 | Shukla et al. | 422/101 |
| 6,814,938 B2 | * | 11/2004 | Karp et al. | 422/100 |
| 6,998,047 B1 | * | 2/2006 | Kopaciewicz et al. | 210/321.75 |
| 7,276,158 B1 | * | 10/2007 | Shukla et al. | 210/198.2 |
| 7,279,134 B2 | * | 10/2007 | Chan et al. | 422/100 |
| 7,332,347 B2 | * | 2/2008 | Li et al. | 436/177 |
| 2003/0013186 A1 | * | 1/2003 | Martin et al. | 435/287.2 |
| 2003/0027354 A1 | * | 2/2003 | Geli | 436/178 |
| 2004/0053422 A1 | * | 3/2004 | Chan et al. | 436/180 |
| 2004/0072375 A1 | * | 4/2004 | Gjerde et al. | 436/541 |
| 2004/0224425 A1 | * | 11/2004 | Gjerde et al. | 436/518 |
| 2005/0069459 A1 | * | 3/2005 | Ahn et al. | 422/100 |
| 2006/0201881 A1 | * | 9/2006 | Marcus et al. | 210/638 |
| 2007/0036685 A1 | * | 2/2007 | Bakry et al. | 422/101 |
| 2007/0248500 A1 | * | 10/2007 | Pawliszyn et al. | 422/101 |

* cited by examiner

*Primary Examiner*—Brian R. Gordon
(74) *Attorney, Agent, or Firm*—Rabin & Berdo, P.C.

(57) ABSTRACT

A solid-phase nano extraction device includes an extraction tube whose inner surface has a nanostructure for a large contact area with object to be detected. The nanostructure can adsorb objects in an extremely short reaction time. A driving structure is designed for the solid-phase micro extraction device. The extraction tube is connected to the driving structure for the objects to enter the fiber under the force of concentration gradient, pressure difference, or capillary force, thereby being adsorbed onto the nanostructure.

10 Claims, 5 Drawing Sheets

SOLID-PHASE NANO EXTRACTION DEVICE

BACKGROUND OF THE INVENTION

1. Field of Invention

The invention relates to an extraction device and, in particular, to a solid-phase micro extraction device.

2. Related Art

When analyzing organic components of a complex sample, one often uses such techniques as liquid-liquid extraction, solid-phase extraction (SPE), and super-phase extraction (SFE). However, these methods have different kinds of defects, such as high costs, complicated operations, long operation time, or pollution of organic solvents poisonous to human bodies. The traditional solid-phase micro extraction (SPME) developed according to the SPE has the advantages of a shorter sample processing time in the sample pretreatment, simpler operation steps, reduced organic solvent uses, and reduced loss of analyzed materials.

This invention develops a novel solid-phase nano extraction (SPNE) device that overcomes defects in conventional sample pretreatment technology. It does not need any solvent and complicated devices. It can directly extract volatile and nonvolatile compounds from aqueous and gaseous samples. The sampling in this method uses a SPNE fiber assembly, which consists of a holder and a fiber. FIG. 1 shows a conventional SPNE fiber assembly. The holder 10 includes a handheld bar 11, a push rod 12, and an adjustable depth gauge 13. The rear end of the handheld bar 11 is connected to the push rod 12 to control the action of a Z-shaped connection rod 14 inside the handheld bar 11. The front end of the handheld bar 11 is connected to the depth gauge 13. The front end of the depth gauge 13 is connected to the fiber 20. The fiber 20 contains a probe 21 whose front tip is a fused-silica rod probe 21 with a diameter of about 0.5 mm, and it is surrounded by a hollow stainless tube 22. The surface of the fused-silica rod used for extraction is coated with a compound layer of PDMS and adsorbing materials. Through the driving of the Z-shaped connection rod 14 connected to the push rod 12, the probe 21 is controlled by the push rod 12 to push out or pull in. When sampling, the user pushes the push rod 12 so that the front fused-silica rod of the probe 21 is exposed in the sample. The probe retracts after finishing sampling. The SPNE fiber assembly is installed in an analyzing apparatus, such as a gas chromatography (GC) or a high performance liquid chromatography (HPLC). The probe extends into the analyzing apparatus for departure in order to complete subsequent analyses.

SUMMARY OF THE INVENTION

In view of the foregoing, the disclosed SPNE device can achieve faster sampling with the design of an extraction tube.

To achieve the above objective, the disclosed SPNE device includes an extraction tube whose inner surface has nanostructure with high specific surface area, consisting of nanotubes, a nano-porous thin film or layered nanospheres. The nanostructure is employed to provide a large contact area with the sample in order to adsorb the sample within an extremely short reaction time. In addition, the SPNE device includes a driving structure connected to the extraction tube. Thus, the sample enters the extraction tube by the driving force of concentration gradient, pumping, pressure difference, and capillary force, thereby being adsorbed onto the nanostructure.

Another objective of the invention is to design a SPNE device with a simple structure, high stability, and easy operations. It can effectively improve the sampling speed and adsorbing quantity of the sample.

The disclosed SPNE device consists of an extraction tube, an outer cylinder, a sealing piston, and a pushing component. The extraction tube is fixed in the outer cylinder and extends out from the front end of the outer tube. The sealing piston is disposed at the front end inside the outer tube, thus forming an airproof space. The airproof space is in communication with the extraction tube. The pushing component pushes against the sealing piston from the rear end of the outer tube. The motion of the pushing component can push or release the sealing piston, thereby changing the size of the airproof space to generate a pressure difference. The sample is thus driven into the extraction tube.

In the pressure gradient structure consisted of the outer tube, the sealing piston, and the pushing component, the airproof space between the sealing piston and the outer tube shrinks when the pushing component pushes the sealing piston. When the pushing component releases the sealing piston, the airproof space becomes larger so that the pressure inside the airproof space is smaller than the ambient space. The sample is thus driven into the extraction tube.

BRIEF DESCRIPTION OF THE DRAWINGS

The invention will become more fully understood from the detailed description given hereinbelow illustration only, and thus are not limitative of the present invention, and wherein.

DETAILED DESCRIPTION OF THE INVENTION

The disclosed SPME device is featured in the use of an extraction tube as the fiber. Its inner surface has a large area of nanostructure to increase the contact are between the nanostructure and the sample. Therefore, the nanostructure can adsorb samples within an extremely short reaction time.

Figure 1:
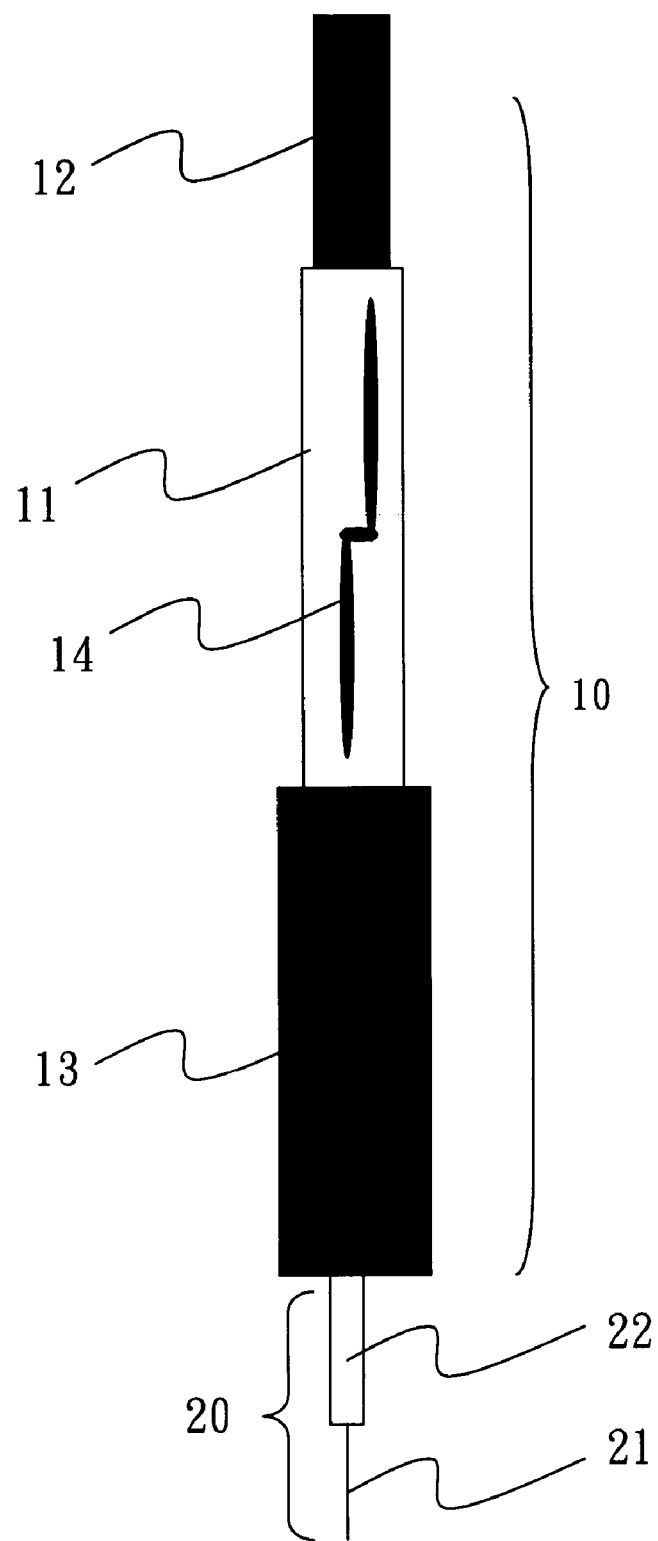
FIG. 1 is a schematic view of a conventional SPME fiber set.
Figure 2A:
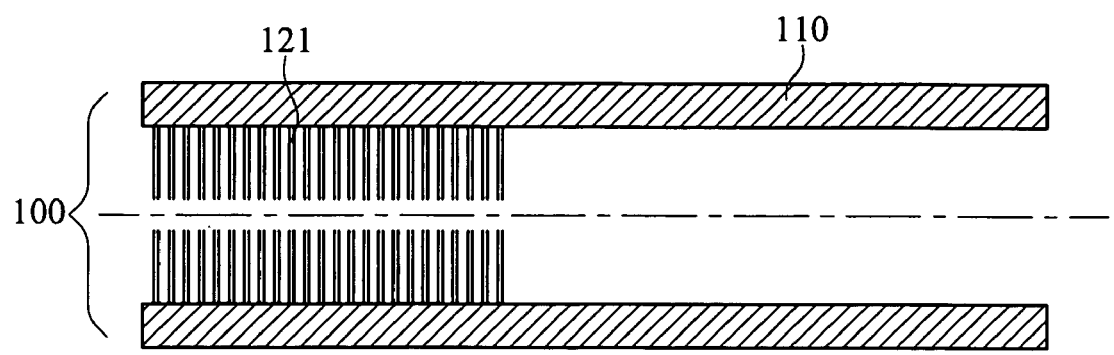
FIGS. 2A to 2C are schematic views of various embodiments of the disclosed extraction tube.
Figure 2B:
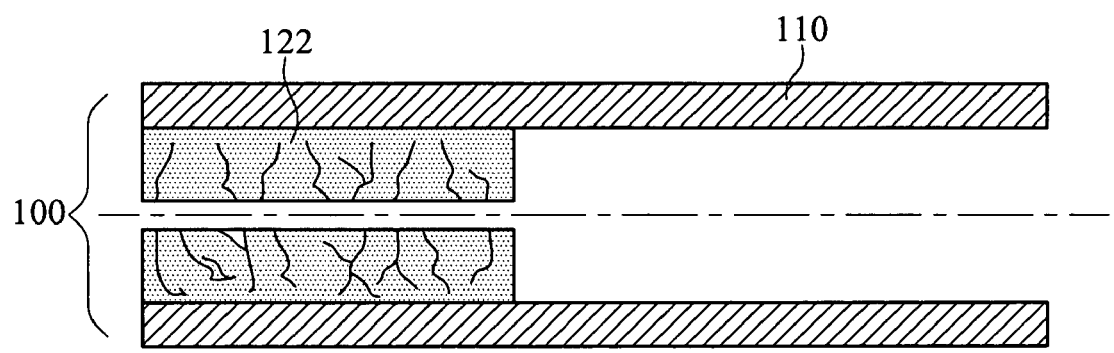
Figure 2C:
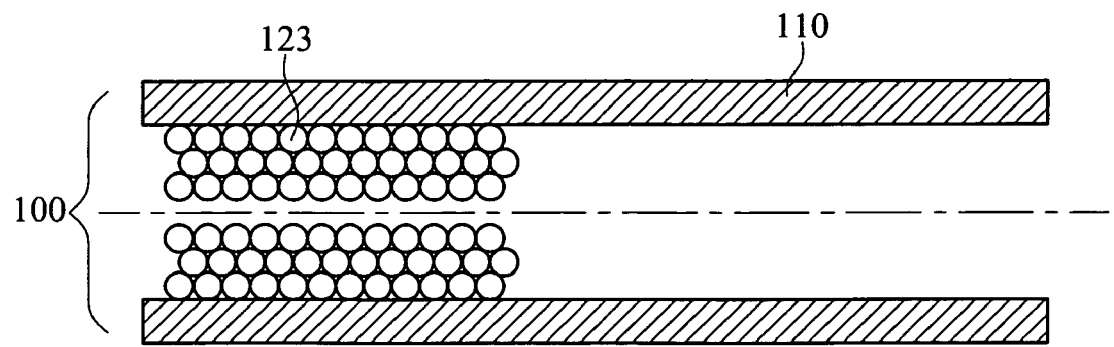

The nanostructure on the inner surface of the extraction tube can be nanotubes/fibers, a nano-porous thin film, or layered nanospheres. Various embodiments of the extraction tube are shown in FIGS. 2A to 2C. As shown in FIG. 2A, the extraction tube 100 is a hollow stainless tube 110, whose inner surface is formed with a hollow carbon nanotube array 121. Since the carbon nanotube has a hollow structure, it has a high BET surface area to adsorb samples. The diameter of the carbon nanotube can be micro-porous, meso-porous, and macro-porous ranging from 1 nm to 500 nm, as defined by the International Union of Pure and Applied Chemistry (IUPAC). The hollow nature of the carbon nanotube is used to sample and detect molecules of different sizes. In other words, one can control the size of the carbon nanotube in order to exclusively allow small molecules to enter.

As shown in FIG. 2B, the extraction tube 100 consists of a nano-porous thin film 122 on the inner surface of a hollow stainless tube 110. The size of the nanoholes can be micro-porous, meso-porous, and macro-porous ranging from 1 nm to 500 nm. As shown in FIG. 2C, the extraction tube 100 consists of a layered nanospheres 123 on the inner surface of a hollow stainless tube 110. The size of the nanospheres is between 1 nm and 500 nm. To increase the selectivity of the extraction tube on the adsorbed materials, the invention can process the nanostructure on the inner surface of the extraction tube (e.g. implanting functional groups) to increase the sensitivity of the nanostructure on certain samples.

The invention further includes a driving structure in the SPNE device so that the samples can enter the extraction tube under the driving force of the concentration gradient, pressure difference, pumping gas or capillary force, thereby being adsorbed onto the nanostructure. Its value is increased by employing a design of easy assembly, simple structure, and high stability.

Figure 3:
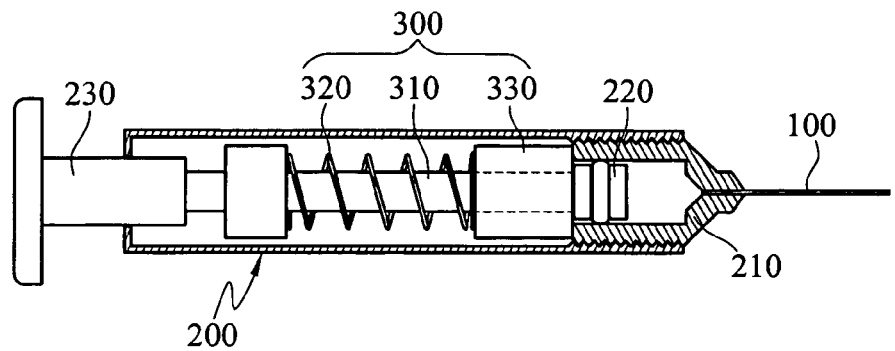
FIG. 3 is a schematic view of the disclosed SPNE device in an embodiment of the invention.

With reference to FIG. 3, the SPNE device is comprised of an extraction tube 100, a fixing pipe 210, an outer tube 200, a sealing piston 220, and a pushing component 300. The extraction tube 100 is fixed by the fixing pipe 210 on the outer tube 200 and extends out from the front end of the outer tube 200. The sealing piston 220 is accommodated at the front end inside the outer tube 200, forming an airproof space with the outer tube 200. The airproof space is in communication with the extraction tube 100. The pushing component 300 pushes against the sealing piston 220 from the rear end of the outer tube 200. This is the driving structure of the extraction tube 100. By advancing or retracting the pushing component 300, the sealing piston 220 is pushed or released. The size of the airproof space is thus changed to produce a pressure difference, driving the samples into the extraction tube 100.

As shown in FIG. 3, the pushing component consists of a push rod 310, a spring 320, and a spring fixing set 330. The push rod 310 pushes against the sealing piston 220. The spring 320 is installed on the spring fixing set 330, which is connected to the push rod 310. When a pressure is imposed on the push rod 310, the sealing piston 220 is pushed tightly against the spring. When the push rod is released, the restoring force of the spring 320 releases the sealing piston 220, thereby producing a pressure difference. In an embodiment of the invention, the SPME device further includes a pressure button 230, whose one end is connected to the pushing component 300 inside the outer tube 200 and whose other end extends out of the outer tube 200. Thus, the user can directly press or release the pressure button to operate the pushing component.

Figure 4:
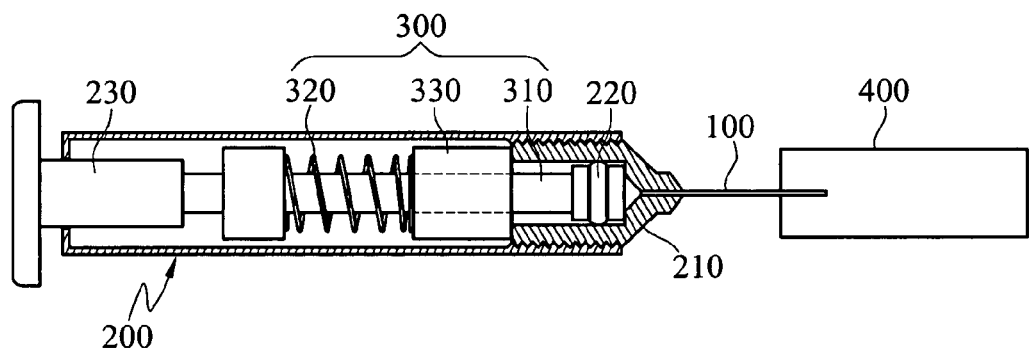
FIGS. 4 and 5 are schematic views of the SPME device in use.
Figure 5:
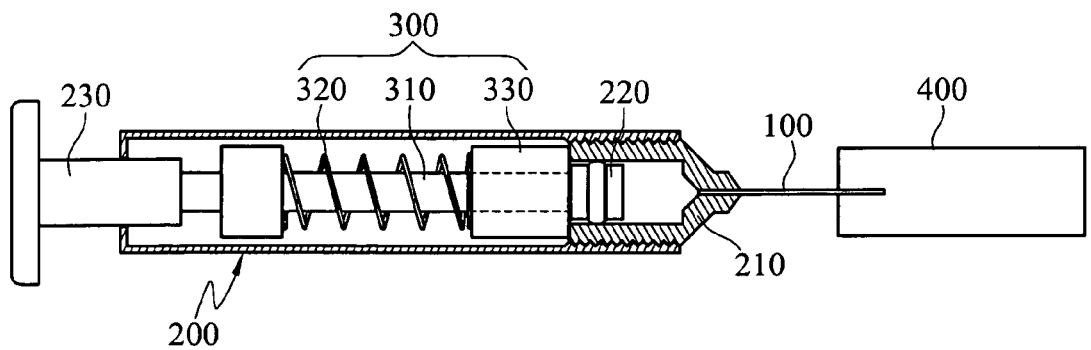

Please refer to FIGS. 4 and 5 for an explanation of the operation of the SPME device. As shown in FIG. 4, the extraction tube 100 is first put into a sample room 400 for sample extraction. One then presses the pressure button 230 for the pushing component to provide a pressure to push the sealing piston 220, diminishing the airproof space between the sealing piston 220 and the outer tube 200. As shown in FIG. 5, the pressure button 230 is released. The restoring force of the spring 320 pulls the push rod to release the sealing piston 220, enlarging the airproof space. At this moment, the pressure in the airproof space is smaller than the sample room 400. Therefore, samples are driven by a sucking force into the extraction tube 100.

Figure 6:
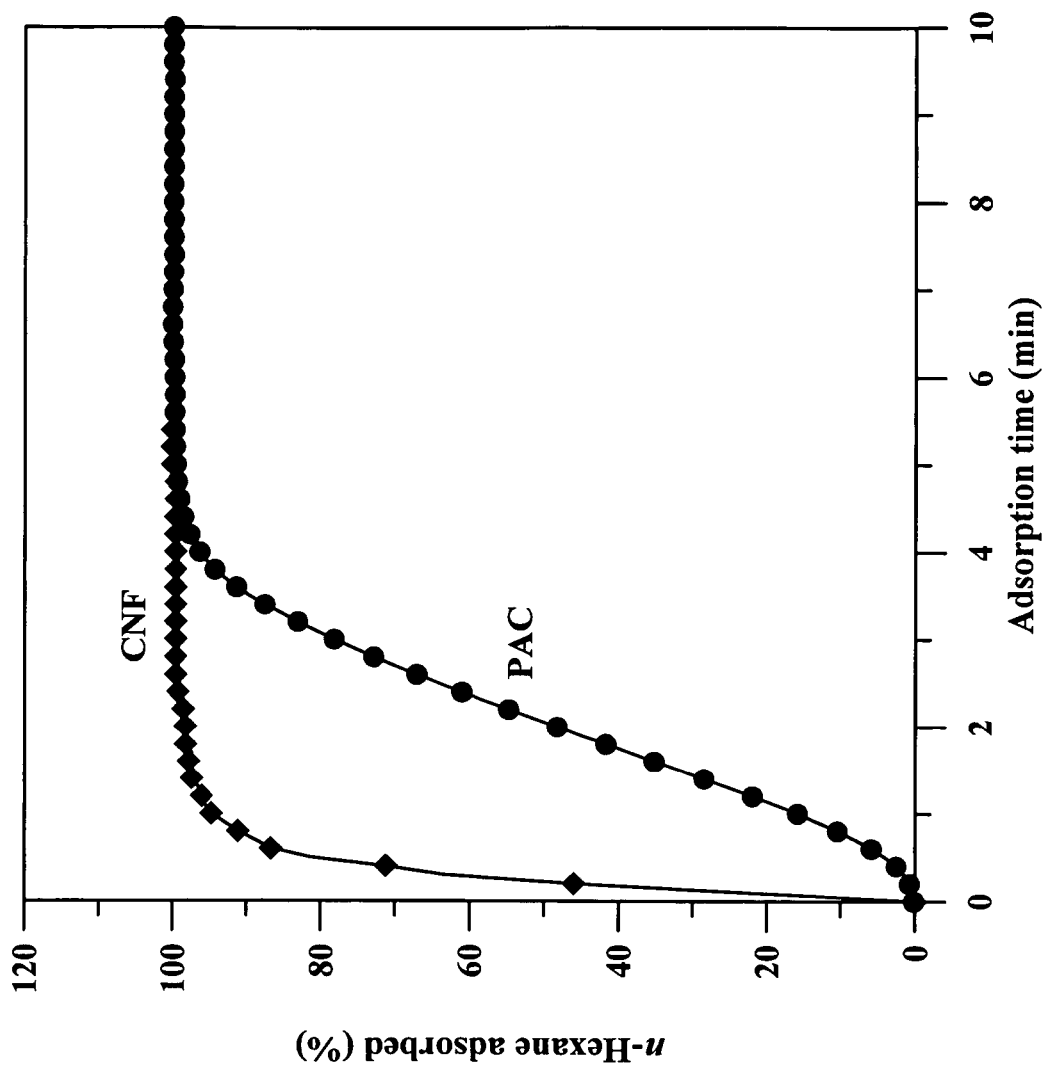
FIG. 6 is a isothermal adsorption rate diagram of the carbon nanotube array and a commercial active carbon film.

To prove that the nanostructure has good adsorption rate and quantity for the samples, we test the physical adsorbing ability of nanomaterials. In this embodiment, the extraction tube uses a carbon nanotube array as the adsorbing material. We compare the disclosed carbon nanotube with the commercial active carbon film (Calgon Inc. Ltd, F300), testing their adsorbing ability of hexane. The BET surface area of the carbon nanotube is 200 to 1500 $m^2/g$. The gap volume is 0.1 to 1.5 $cm^3/g$. The experimental result is shown in FIG. 6. It shows the isothermal adsorption rates of the carbon nanotube array and the commercial active carbon film. It proves that the special nanostructure (with a hollow nanofiber array) can quickly achieve adsorption equilibrium, thus increasing the extraction rate.

Figure 7:
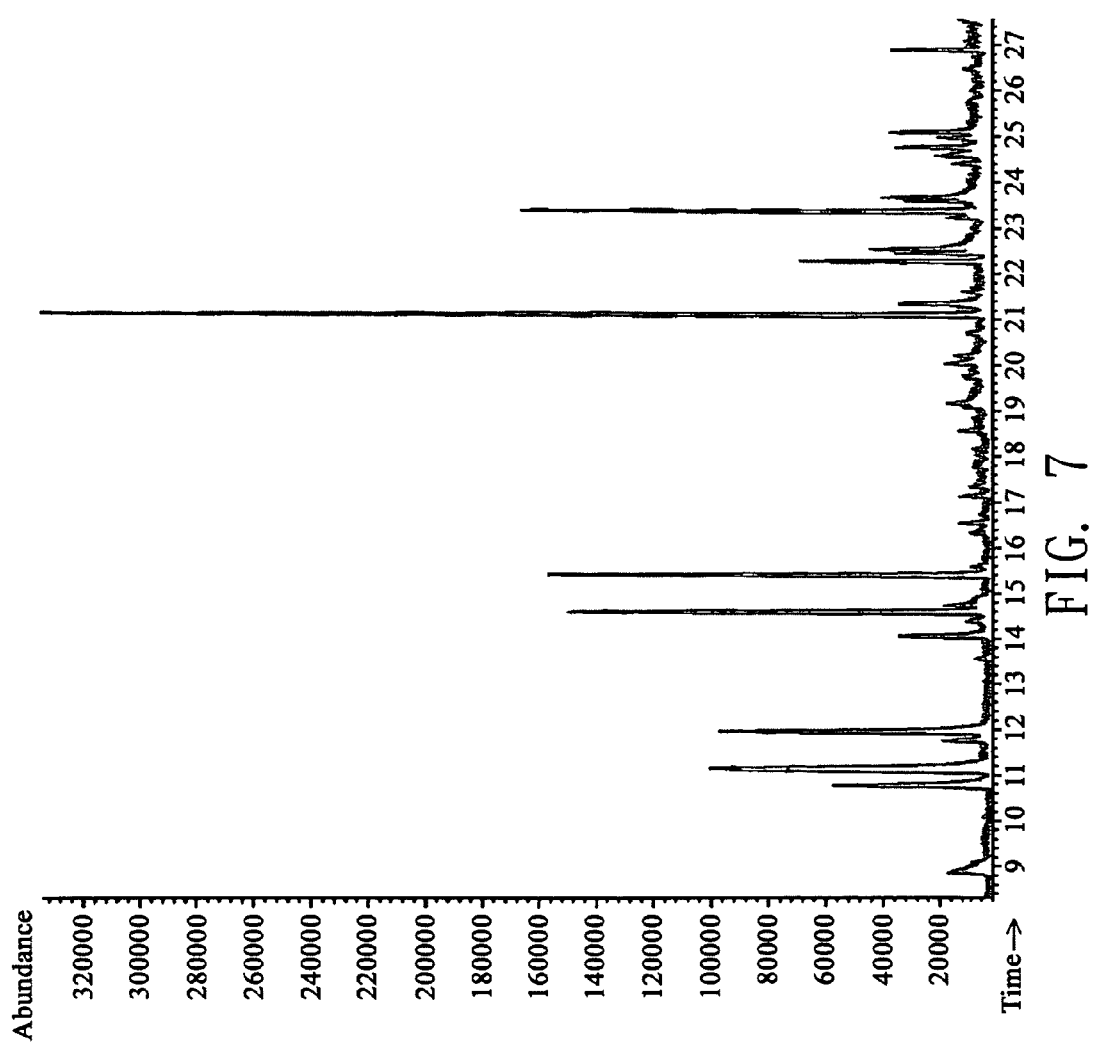
FIG. 7 is a gaseous chromatography spectrum of the disclosed SPME device in an embodiment.

We use FIG. 7, the gaseous chromatography spectra, to show the extraction effect of the disclosed SPME device. The tested samples are ethylbenzene, 1,3-dimethyl-benzene, 1,2, 5-trimethyl-benzene, 1,3,5-trimethyl-benzene, and naphthalene. The experimental results show that the disclosed SPME device has a very good extraction effect for above-mentioned five volatile benzene compound.

Certain variations would be apparent to those skilled in the art, which variations are considered within the spirit and scope of the claimed invention.

What is claimed is:

1. A solid-phase nano extraction (SPNE) device for extracting a sample, comprising:
    an extraction tube with an inner surface having a nanostructure with high specific surface area;
    an outer tube, wherein the extraction tube is fixed in the outer tube and extends out from a front end of the outer tube;
    a sealing piston, which is accommodated in the front end inside the outer tube to form an airproof space with the outer tube, the airproof space being in communication with the extraction tube; and
    a pushing component, which pushes against the sealing piston from the rear end of the outer tube to push and pull the sealing piston and thereby changes the size of the airproof space to produce a pressure difference, which drives the sample into the extraction tube;
    wherein an airproof space between the sealing piston and the outer tube reduces as the pushing component pushes the sealing piston, and the airproof space between the sealing piston and the outer tube increases as the pushing component releases the sealing piston, the pressure in the airproof space is thus smaller than the ambient space of the extraction tube, thereby driving the sample into the extraction tube.

2. The SPNE device of claim 1, wherein the nanostructure is a carbon nanotube array.

3. The SPNE device of claim 2, wherein the diameter of the nanotube in the carbon nanotube array ranges among microporous, meso-porous, macro-porous, from 1 nm to 500 nm.

4. The SPNE device of claim 1, wherein the nanostructure is a nano-porous thin film with a plurality of nanoholes.

5. The SPNE device of claim 4, wherein the diameter of the nanoholes ranges among micro-porous, meso-porous, macro-porous, from 1 nm to 500 nm.

6. The SPNE device of claim 1, wherein the nanostructure is a plurality of layered nanospheres.

7. The SPNE device of claim 6, wherein the diameter of the layered nanospheres is between 1 nm and 500 nm.

8. The SPNE device of claim 1 further comprising a fixing pipe, wherein the extraction tube is fixed on the outer tube by the fixing pipe and extends out from the front end of the outer tube.

9. The SPNE device of claim 1, wherein the pushing component comprising a push rod, a spring and a spring fixing set, wherein the push rod pushes against the sealing piston, the spring is installed in the spring fixing set, the spring fixing set is connected to the push rod, and the spring provides a restoring force to pull back the push rod, thereby releasing the sealing piston.

10. The SPNE device of claim 1 further comprising a pressure button, whose one end is connected to the pushing component in the outer tube and whose other end extends out of the outer tube.

* * * * *